(12) United States Patent
Maddry et al.

(10) Patent No.: US 6,251,930 B1
(45) Date of Patent: Jun. 26, 2001

(54) ACTIVATING Cl⁻ SECRETION

(75) Inventors: Joseph A. Maddry; Eric J. Sorscher, both of Birmingham, AL (US)

(73) Assignees: Southern Research Institute; UAB Research Foundation, both of Birmingham, AL (US)

( * ) Notice: Subject to any disclaimer, the term of this patent is extended or adjusted under 35 U.S.C. 154(b) by 0 days.

(21) Appl. No.: 09/529,915

(22) PCT Filed: Oct. 23, 1998

(86) PCT No.: PCT/US98/22369

§ 371 Date: Apr. 21, 2000

§ 102(e) Date: Apr. 21, 2000

(87) PCT Pub. No.: WO99/20294

PCT Pub. Date: Apr. 29, 1999

Related U.S. Application Data
(60) Provisional application No. 60/063,222, filed on Oct. 23, 1997.

(51) Int. Cl.⁷ .............................................. A61K 31/4164
(52) U.S. Cl. ............................................ 514/398; 514/851
(58) Field of Search ...................... 514/851, 398

(56) References Cited

U.S. PATENT DOCUMENTS

| | | | |
|---|---|---|---|
| 5,618,792 | 4/1997 | Gyorkos et al. | 514/18 |
| 5,635,160 | 6/1997 | Stutts, III et al. | 424/45 |

FOREIGN PATENT DOCUMENTS

WO 96/18385   6/1996   (WO) .

OTHER PUBLICATIONS

Cliff et al., Am. J. Physiol., 262(5, Pt. 1), C1154–1160 (abstract), 1992.*

* cited by examiner

*Primary Examiner*—Phyllis G. Spivack
(74) *Attorney, Agent, or Firm*—Connolly Bove Lodge & Hutz

(57) ABSTRACT

Diazoimidazole compounds for activating Cl-secretion are disclosed that can be used for treating cystic fibrosis.

10 Claims, 16 Drawing Sheets

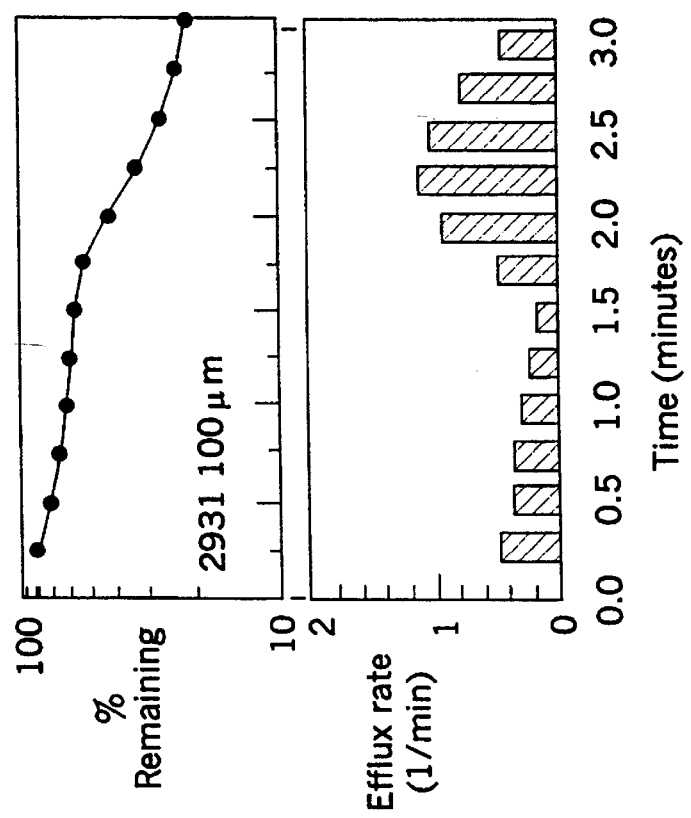
FIG. 1E
FIG. 1F
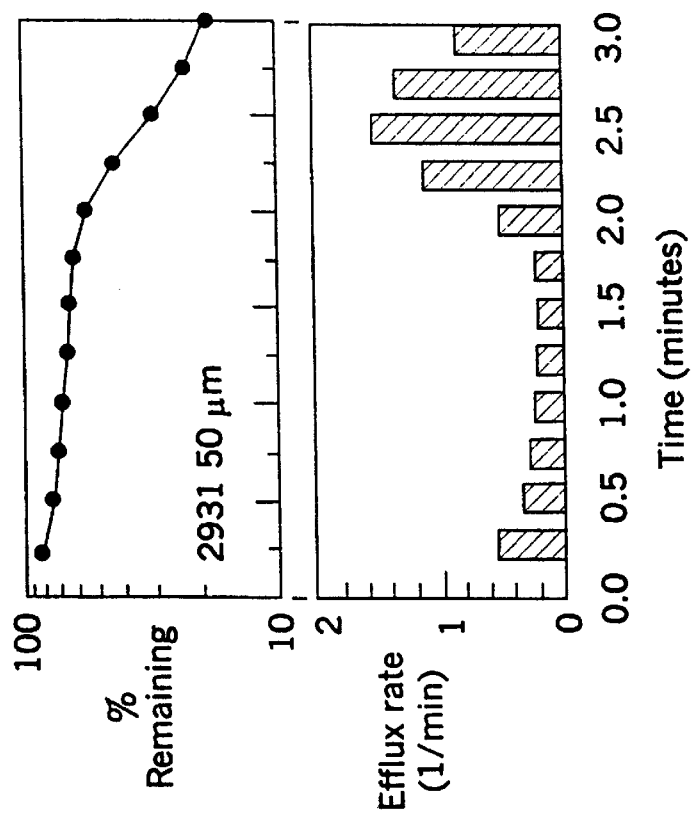

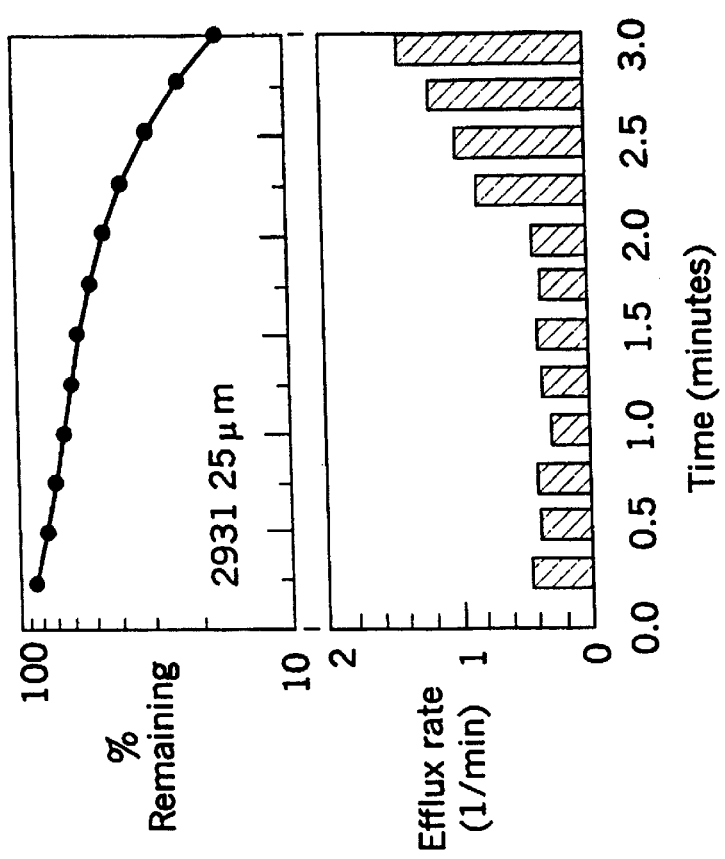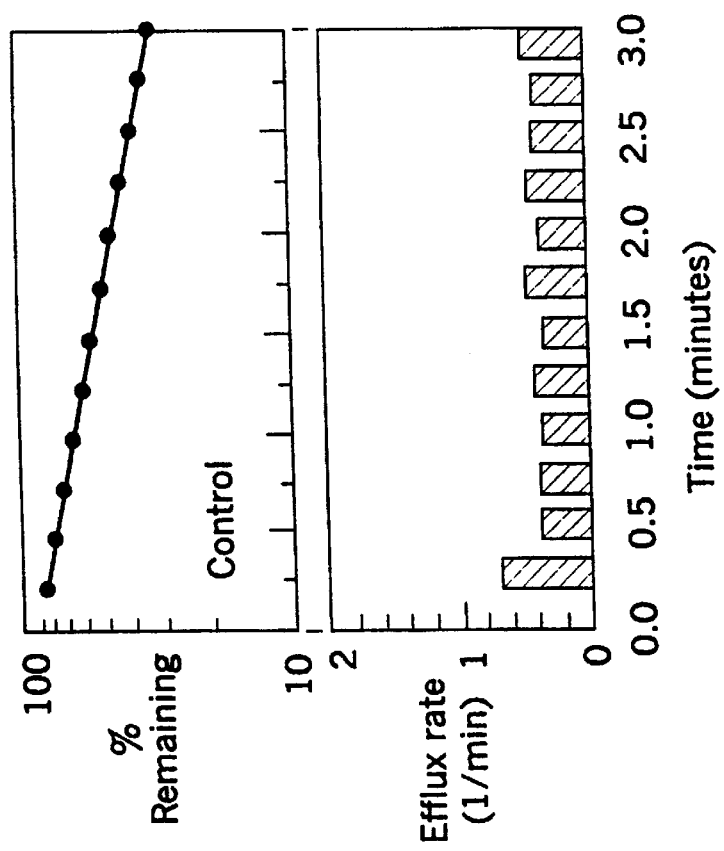

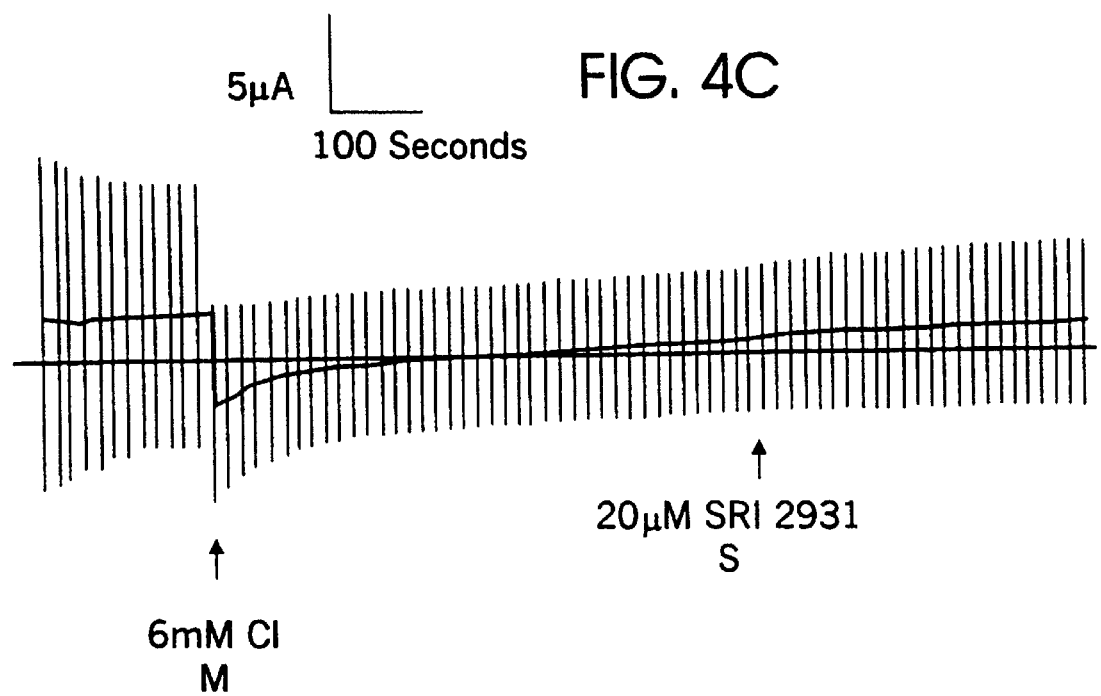
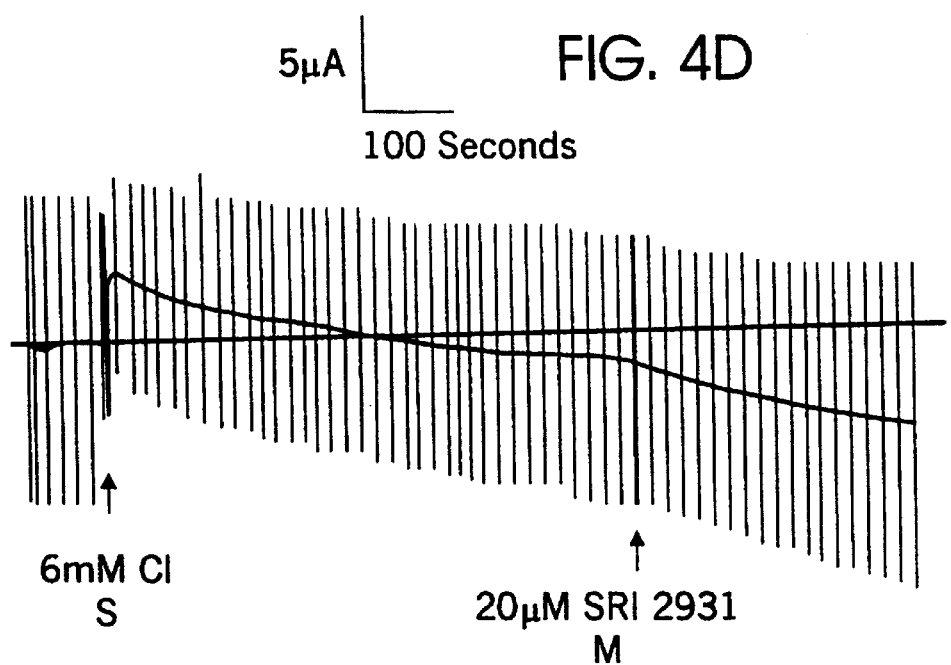

ACTIVATING Cl⁻ SECRETION

This Appln is a 371 of PCT/US98/22369 filed Oct. 23, 1998, which claims the benefit of 60/063,222 filed Oct. 23, 1997.

DESCRIPTION

1. Technical Field

The present invention is concerned with activating Cl⁻ secretion in a patient. More particularly the present invention is especially concerned with treating patients suffering from cystic fibrosis by administering certain heterocyclic nitrogen containing compounds.

2. Background of Invention

Insufficient Cl⁻ transport in epithelial cells has been associated with disease in individuals and especially with cystic fibrosis. In particular, the cystic fibrosis transmembrane conductance regulator (CFTR) functions as a Cl⁻ channel. At the surface of epithelial cells, it also regulates the activity of other ion channels, including amiloride-sensitive Na⁺ channels, and other Cl⁻ transport pathways. Cystic fibrosis mice lack Cl⁻ transport capabilities in their nasal airways, lung cells, and intestines. In human with cystic fibrosis, sweat ducts cannot properly reabsorb Cl⁻. It has also been suggested that the Pseudomonas predisposition in cystic fibrosis patients may be associated with defects in Cl⁻ reabsorption, rather than secretion. These results collectively point to defects in Cl⁻ transport as responsible for pathogenesis in the disease.

CFTR regulates airway Na⁺ re-absorption through effects on epithelial sodium channels (ENaCs). CFTR may also regulate K⁺ channels. Several studies have indicated important effects of wild-type CFTR on membrane turnover in epithelia, including regulation of both endo- and exocytosis. Acidification of intracellular compartments such as the golgi and proper in protein glycosylation and sialation have also been suggested to rely on normal CFTR function. Although CFTR may subserve other functions in epithelia, defective Cl⁻ secretion into the airways is the best understood and most likely physiologic contributor to clinical disease. Nasal and lower airway potential difference measurements include abnormal Cl⁻ secretion into CF airways. Correction of Cl⁻ secretory defects are viewed as important and possibly the benchmark by which to evaluate the effectiveness of therapeutic interventions such as gene-based or other pharmacologic therapies. Cystic fibrosis mice are believed to be protected from lung disease because of alternate Cl⁻ secretory pathways that are not found in the intestinal tracts of these animals, accounting for the absence of lung disease in the animal model. The absence of alternate Cl⁻ secretory pathways in murine intestines of mice may explain the predisposition of CF mice towards lethal gastrointestinal pathophysiology. Finally, genetic modifiers than lessen the severity of disease in CF mice appear to activate alternate Cl⁻ secretory pathways in the intestines of these animals. Because of a preponderance of evidence that Cl⁻ secretion is not only associated with CF, but directly responsible for the disease, Cl⁻ secretagogues form an important aspect of new pharmacologic approaches to treatment.

Scientific efforts directed towards identifying activators of Cl⁻ secretion in CF tissues are an important aspect of drug discovery in the disease. Important evidence indicates that drugs in the sulfonylurea class can maintain certain K⁺ channels in a tonically open-state. Channel openers that might have comparable action on CFTR or other Cl⁻ transport pathways are being actively sought as part of therapeutic development in the disease. In principal, such agents might either activate residual CFTR activity at the cell surface, open alternate Cl⁻ secretory pathways, or increase the gradient for apical Cl⁻ secretion from cells, for example by opening basolateral K⁺ channels and augmenting the tendency for Cl⁻ to exit at the apical surface.

Nucleotides such as uridine triphosphate (UTP) and adenosine triphosphate (ATP) have been shown to activate Cl⁻ secretion in CF tissues, including transepithelial transport in vivo. These drugs also transiently correct CF bioelectric abnormalities, and cause strong Cl⁻ secretion as judged by in vivo measurements of airway potential difference. However, drugs such as UTP are rapidly cleared at the airway cell surface by endogenous ectonucleotidases, and therefore may have limited bioavailability in vivo. Moreover, the activities of compounds such as UTP are often short lived, and disappear within minutes unless fresh compound is continuously provided on to airway epithelium in vivo. Tachyphylaxis to UTP has been observed both in vitro and in vivo.

The drug CPX, a cyclopropyl xanthene, appears to directly activate ΔF508 CFTR. CPX exhibits this activity in human CF pancreatic cells (CFPAC—cell line), in airway cells derived from a CF patient (IB3-1—cell line), and in NIH 3T3 cells after expression of the ΔF508 protein. In all cases, Cl⁻ efflux from these cells could be activated by CPX. Because CPX is believed to bind and activate ΔF508 CFTR at the cell surface, the drug may only be active if sufficient ΔF508 CFTR is present in the plasma membrane to permit induction of Cl⁻ transport. Previous studies have suggested that levels of ΔF508 CFTR present at the cell surface could be extremely low in vivo due to recognition of the ΔF508 mutation by protein processing mechanisms in the endoplasmic reticulum that rapidly degrade the ΔF508 protein.

In general, Cl⁻ secretagogues act by elevating intracellular levels of either $Ca^{2+}$ or cyclic AMP (cAMP). For example, agents such as UTP, ATP, NS004, and duramycin are believed to activate secretion in CF tissues by elevating cellular $Ca^{2+}$. Drugs such as adenosine and milrinone activate residual CFTR activity by signaling through cAMP and PKA.

SUMMARY OF INVENTION

The present invention is concerned with drugs that exhibit high activity and long-lived activity for activating Cl⁻ secretion from CF airway and pancreatic cells and across cystic fibrosis tissues and cell monolayers.

Compounds employed according to the present invention provide relatively stable activation of Cl⁻ secretion in CF cells and tissues and appear to work by a mechanism independent of either intracellular $Ca^{2+}$ or cAMP. Compounds employed according to the present invention elicit Cl⁻ secretion that is active in CF and normal epithelia, and do not appear to require ΔF508 CFTR at the cell surface.

The present invention is concerned with promoting or activating Cl⁻ secretion in a patient in need thereof by administering to the patient a composition comprising a pharmaceutically acceptable carrier and an amount effective for promoting or activating Cl⁻ secretion of a compound represented by the formula:

wherein A is a 5 or 6 membered unsaturated heterocyclic ring containing at least one N atom;

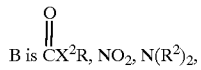

$X^2$ is O, NH, NR,
  each R individually is alkyl, cycloalkyl, aryl, alkaryl and aralkyl,
  each $R^2$ individually is H, alkyl, cycloalkyl, aryl, alkaryl and aralkyl;

Y is halogen; alkylthio group or nitrogenous moiety.

The present invention is also concerned with treating a patient suffering from cystic fibrosis by administering to the patient a composition comprising a pharmaceutically acceptable carrier and an amount effective for treating cystic fibrosis of a compound represented by the formula:

wherein A is a 5 or 6 membered unsaturated heterocyclic ring containing at least one N atom;

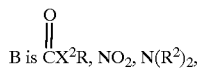

$X^2$ is O, NH, NR,
  each R individually is alkyl, cycloalkyl, aryl, alkaryl and aralkyl,
  each $R^2$ individually is H, alkyl, cycloalkyl, aryl, alkaryl and aralkyl;

Y is halogen; alkylthio group or nitrogenous moiety.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

SUMMARY OF DRAWINGS

FIGS. 1A–1F are graphs of efflux rate.

FIGS. 2A–2C are graphs showing efflux rate of iodide in CF epithelial cells.

FIGS. 4A–4D illustrate transport effect achieved by the present invention.

BEST AND VARIOUS MODES FOR CARRYING OUT INVENTION

Figure 1A:
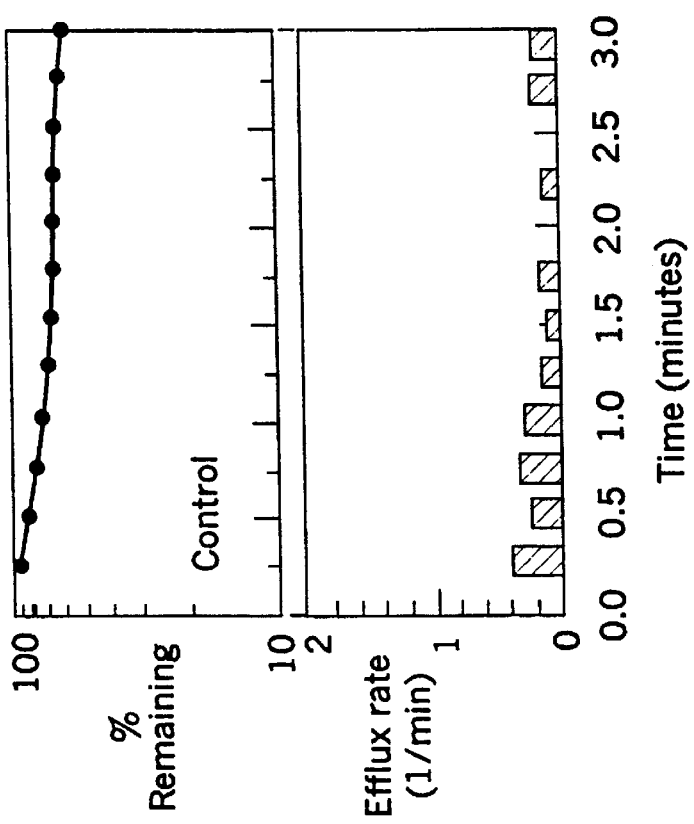
Figure 1B:
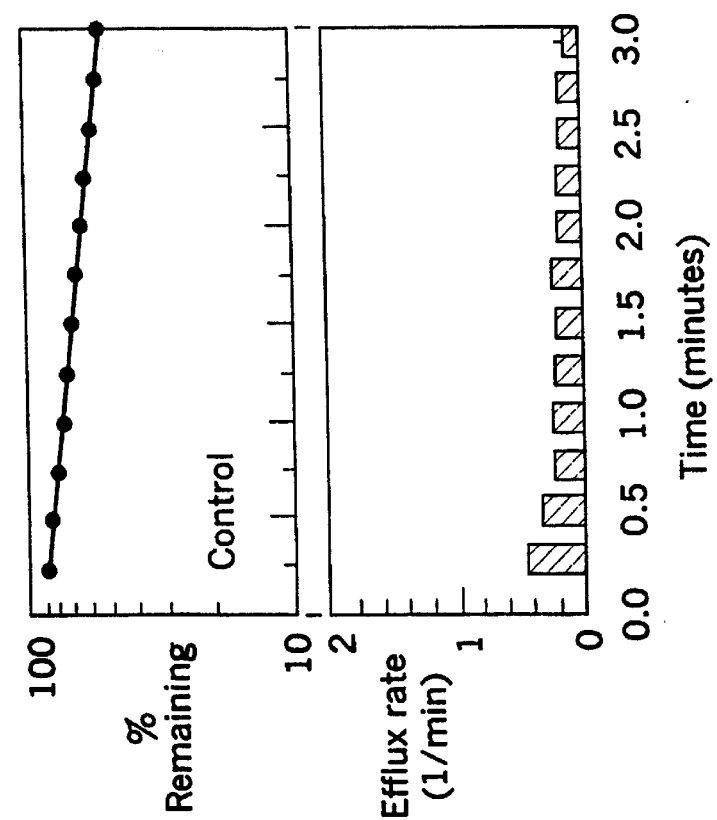
Figure 1C:
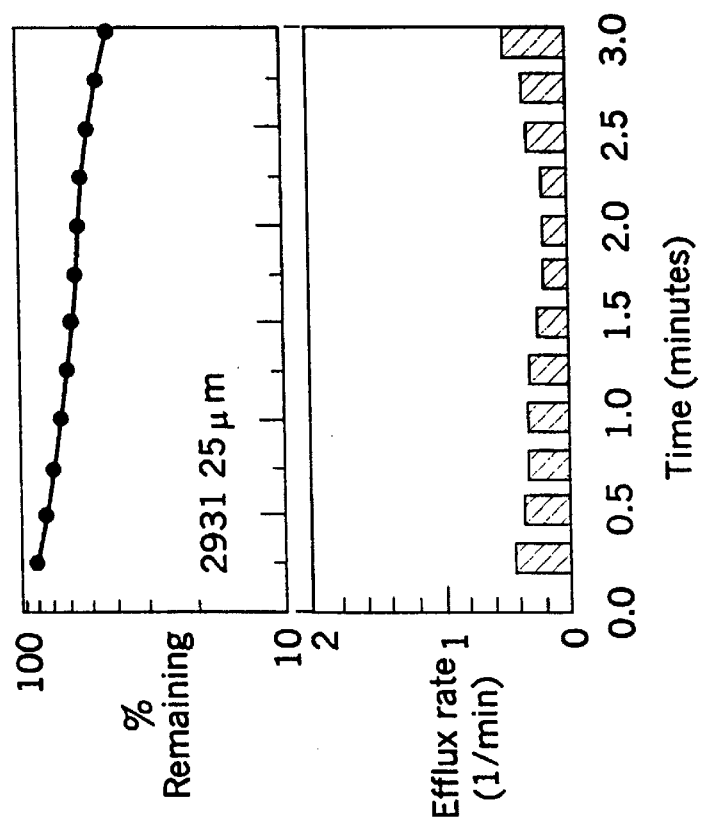
Figure 1D:
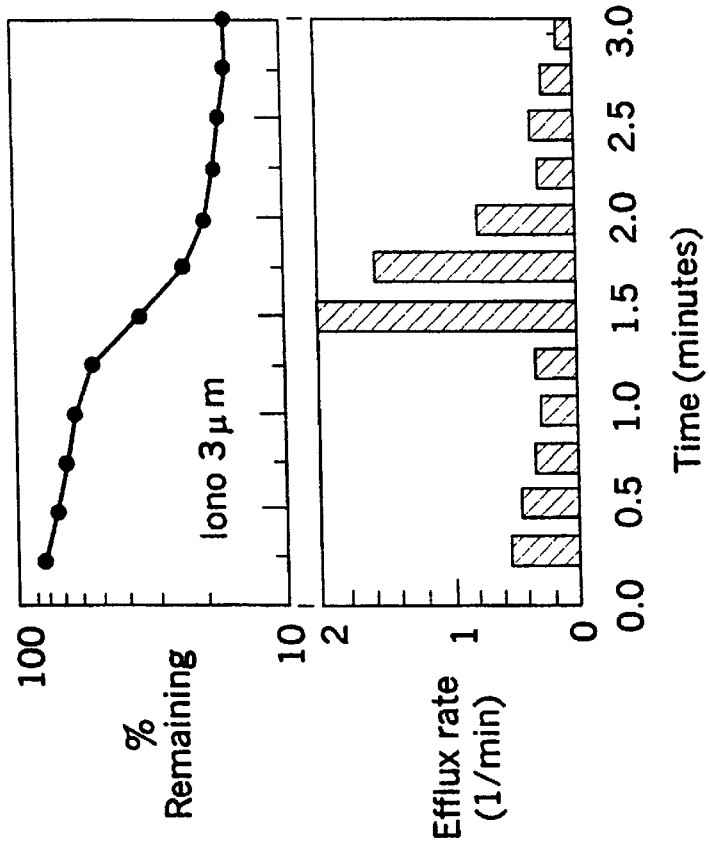

The compounds employed pursuant to the present invention are represented by the following formula:

wherein A is a 5 or 6 membered unsaturated heterocyclic ring containing at least one N atom;

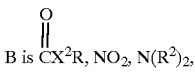

$X^2$ is O, NH, NR,
  each R individually is alkyl, cycloalkyl, aryl, alkaryl and aralkyl,
  each $R^2$ individually is H, alkyl, cycloalkyl, aryl, alkaryl and aralkyl;

Y is halogen; alkylthio group or nitrogenous moiety.

Examples of some suitable 5 or 6 membered single ring groups suitable as the A moiety are

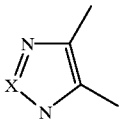

X=N, CH, or CR;

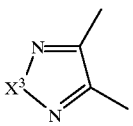

$X^3$=O, or S;

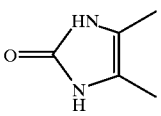

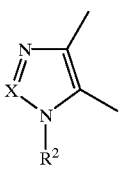

X—N, CH or CR

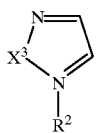

$X^3$=O or S;

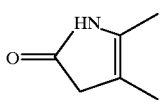

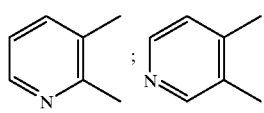

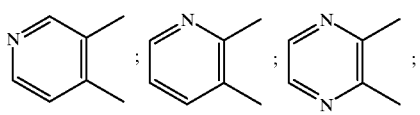

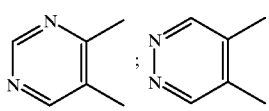

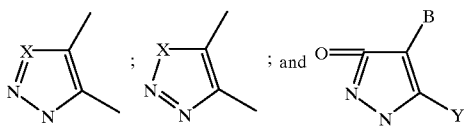

X=N, CH, CR  X=O or S

R and $R^2$ are the same as defined above.

Examples of some suitable nitrogenous moieties for Y are $N_2$, $N_3$, $NO_2$, $NH_2$, CN, NCS, NHR, $N(R)_2$, and N=N—$N(R)_2$. R is the same as defined above.

The alkyl moieties of the R, $R^2$ and Y groups typically contain 1–22 carbon atoms and more typically 1–12 carbon atoms. The cycloalkyl moieties include saturated and unsaturated ring groups such as cyclopropyl, cyclobutyl, cylcopentyl, cyclohexyl, cycloheptyl and cyclooctyl. The aryl moieties of the R and $R^2$ groups typically contain 6 to 14 carbon atoms and 1–3 rings, and more typically 6 carbon atoms. Examples of suitable R and $R^2$ groups are methyl, ethyl, isopropyl, n-butyl, isobutyl, hexyl, hexenyl, octyl, decyl, dodecyl, geranyl, retinyl, phenyl, benzyl and phenethyl. Although the compounds used in the present invention have been represented by the above single formula for purposes of simplicity, it is understood that the electron-rich heterocyclic base of some of the various compounds is mesoionic and can be represented by alternative structural formulae. For example, the preferred compound, 5-diazoimidazale-4-carboxylic acid n-octyl ester is represented by the following formulae:

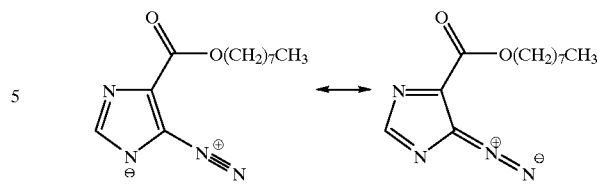

Further compounds according to the present invention are illustrated by the following formulae:

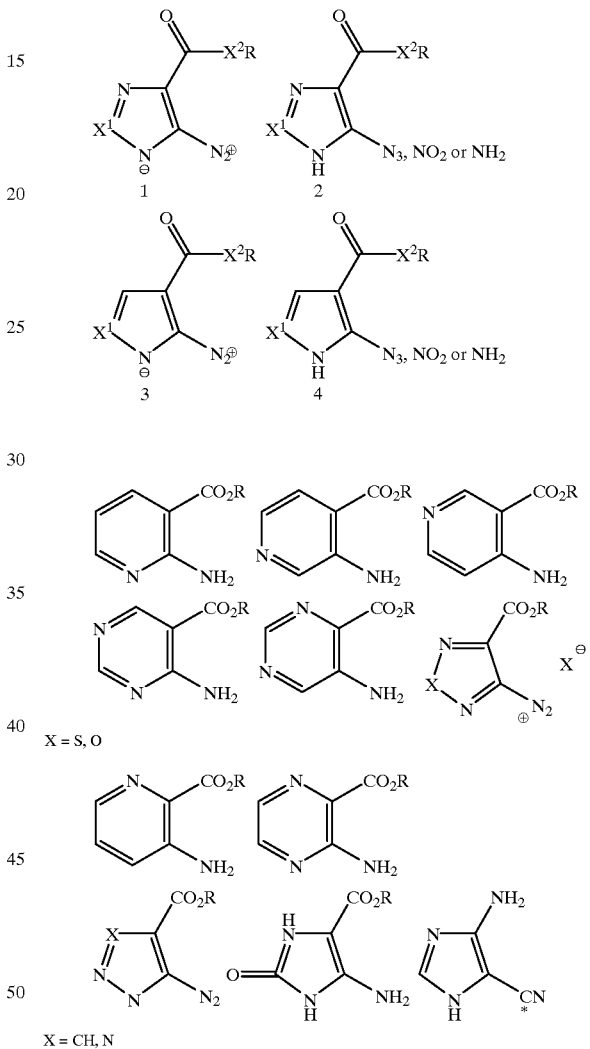

Various of the compounds employed in accordance with the present invention and method of preparing are described in U.S. Pat. No. 3,654,257, the entire disclosure of which is incorporated herein by reference. In addition, Scheme 1 below depicts the synthetic route that was used for preparing 5-diazoimidazol-4-carboxylic acid n-octyl ester (identified in the figures as SRI 2931) and can be used to synthesize various of the disclosed compounds.

In particular, nitration of commercially available imidazole 1 affords 2, which then undergoes an aldol-type condensation to give olefin 3. Oxidative cleavage of the double bond, followed by esterification of the resulting carboxyl moiety with n-octanol, and subsequent reduction of the nitro substituent, provides amine 6, which can be converted to the mesoionic 5-diazoimidazol-4-carboxylic acid n octyl ester using standard diazotization techniques. This same protocol, utilizing alternative alcohols for the esterification of 4, affords compounds of general structure 7.

Scheme 2 below illustrates obtaining compounds having an azido moiety or cyano moiety. The azido analogs are readily available from the parent esters or amides by several procedures, including treatment with hydrazine or thiosemicarbazide. The corresponding nitrile can be obtained from the diazonium species by nucleophilic displacement of the diazonium group.

Scheme 1 below also illustrates the nitro, amino group or substituted amino at ring position 4. The halogen such as fluoro groups can be introduced via a Schiemann reaction of the diazonium species. The isocyanates and isothiocyanates can either be prepared directly from the diazonium salts, or obtained from the azides via modified Staudinger or aza-Wittig reactions. The triazenes at position 4 can be prepared by coupling of the diazoimidazole with an appropriate primary or secondary amine.

Removing hydrogen on the ring can be carried out by substituting the ring nitrogen atom with a lower, non-hydrogen bonding group such as $R^2$=methyl. This can be accomplished by alkylation.

The amides identified inter alia in Scheme 2 (structure 10) can be obtained by amination of the corresponding ester. The ketones (structure 10, $X=CH_2$) can be prepared from intermediates analogous to 3 in Scheme 1. For example, hydroboration of 3 and its analogs with oxidative work-up conditions, followed by further oxidation of the resulting carbinol yield the desired ketones regioselectively.

Scheme 3 shows preparing a radiolabelled form of 5-diazoimidazol-4-carboxylic acid n-octyl ester. The radiolabelled compounds are especially useful in evaluating the studying the mechanism of action of the system.

Scheme 1

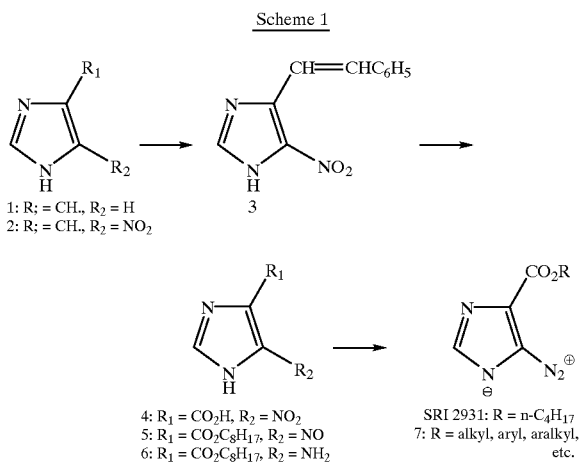

Scheme 2

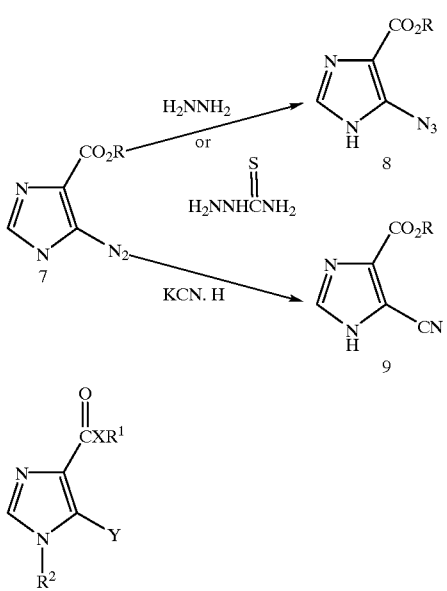

$R^1, R^2$ as in Scheme 1 (alkyl, aryl, etc.)
X = O, NH, $NR^2$
Y = $NO_2$, $NH_2$, halogen, alkylthio, etc.

Scheme 3

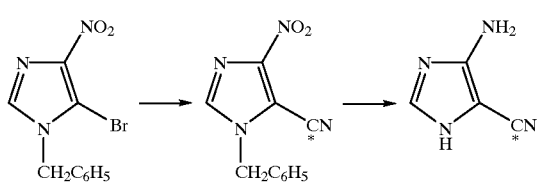

The compounds used according to the present invention can be administered by any means that produces contact of the active agent's site of action with the desired submucosal gland or surface epithelium in the body of a human, mammal, bird, or other animal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; and the frequency of treatment. A daily dosage of active ingredient can be expected to provide about 10 to about 200 μmolar to the lower airways, a typical example being about 100 μmolar.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carries, such as lactose, starch, cellulose, derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols, such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carries are described in Remington's Pharmaceutical Sciences, Mack Publishing Company, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate. 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

In tissue monolayers, the drug leads to stable activation of $Cl^-$ secretion that is well maintained even following removal of drug from the solution bathing the cells. This compound's activity is observed specifically after administration to the apical, and not the basolateral, surface of polarized airway, pancreatic, and colonic epithelial cells.

Test for Activation of Anion Efflux from Cystic Fibrosis Cells

The iodide efflux protocol is a conventional test for the existence of anion permeability pathways, including both CFTR (cAMP-activated) and non-CFTR permeability pathways (e.g., $Ca^{2+}$-activated $Cl^-$ transport). FIG. 1 establishes that 5-diazoimidazol-4-carboxylic acid n-octyl ester (so-called compound "SRI 2931") confers a rapid efflux of iodide in CF epithelial cells similar to that observed in cells containing wild-type CFTR and stimulated by action of cAMP (i.e., T84 colonic carcinoma cells treated with 10 $\mu$M forskolin, data not shown). In addition, this effect of 5-diazoimidazole-4-carboxylic acid n-octyl ester does not appear to be $Ca^{2+}$-dependent, since removal of extracellular $Ca^{2+}$ (a maneuver which depletes both intra- and extracellular $Ca^{2+}$ stores) does not substantially inhibit anion efflux. Ionomycin, a $Ca^{2+}$ ionophore, is known to activate non-CFTR-type anion efflux pathways in CFPAC cells by increasing intracellular $Ca^{2+}$. Ionomycin-mediated anion transport in CFPAC cells was studied and this control indicated the anticipated stimulation of iodide efflux by ionomycin.

Figure 2C:
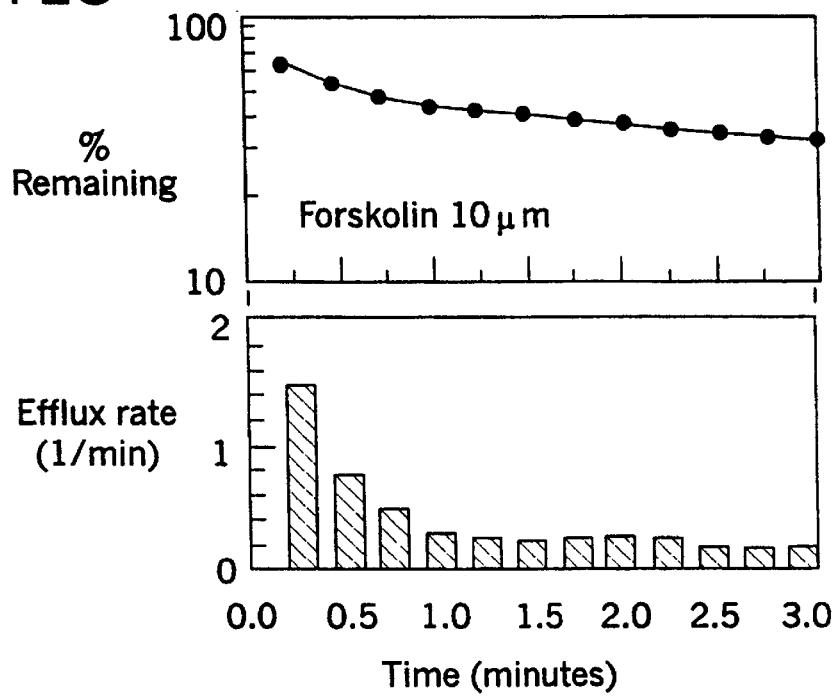

FIG. 2. Anion efflux protocol in human epithelial cells.

Epithelial cells in the pancreatic ducts, lung, and colon secrete fluid and electrolytes into the pancreatic ductular lumen, airways and intestinal lumen, respectively. The inability to secrete anions in response to a cAMP-dependent agonist such as forskolin is a hallmark of the CF phenotype. Note that epithelial cells derived from CF pancreatic ductular cells (FIG. 1), or primary airway cells taken from a CF patient (FIG. 2), lack forskolin-activated anion permeability pathways, since they lack CFTR. Normal human colonic epithelial cells (T84 cells, which express high levels of CFTR) exhibit strong activation of anion efflux due to forskolin (not shown). Iodide efflux is strongly activated in all three cell types by 5-diazoimidazole-4-carboxylic acid n-octyl ester, indicating that these effects are not dependent on the presence of wild-type CFTR. Methods: Iodide efflux. Iodide efflux was performed as previously described (Venglarik et al., *Am. J. Physiol.* 259:C358–C364, 1990, and Drumm et al., *Cell* 62:1227–1233, 1990). Cells were grown on 35 mM culture dishes, and effluxes were performed when the cells were 80–100% confluent using a phosphate buffered Ringer's solution. Cells were loaded with $^{125}I$ (2–5 $\mu$Ci/ml) for 30 minutes and then washed with PBS to remove extracellular $^{125}I$. Efflux was detected by measuring the radioactivity in the extracellular solution which was changed every 15 seconds. At specific points, compounds were added to the cells. Increases in the rate of efflux after addition of a compound indicates the activation of an anion permeability pathway.

FIG. 3. 5-diazoimidazol-4-carboxylic acid n-octyl ester does not increase cellular cAMP and allows proliferation of cells at concentrations that activate anion efflux. (3A) Cell proliferation assay in the presence and absence of 5-diazoimidazole-4-carboxylic acid n-octyl ester.

Proliferation was measured as in Hughes et al., Tumor specific killing with high bystander toxicity using the human tyrosinase promoter to express the E. coli PNP gene, Cancer Research 55: 3339–3345, 1195 and Parker et al., In vivo gene therapy of cancer with E. coli purine nucleoside phosphorylase, Human Gene Therapy, 1997 (in press) using a commercially available kit (Cell titer 96 kit, Promega) and carried out according to manufacturer's protocol. 20 µm 2931 activates Cl⁻ secretion in CF cells within 5 minutes. Even when these cells are grown for 7 days in 2931 at 20 µm, minimal effects on cellular proliferation are observed, and an initial growth delay is overcome by day 7 of the experiment. (FIG. 3A) cAMP levels were tested using the cAMP Immunoassay kit (Cayman) according to manufacturer's protocol.

These results demonstrate 1) the tested diazoimidazole causes anion release from cells lacking functional CFTR, 2) the component works in both human CF pancreatic cells and human airway cells, 3) the drug is active in both a cell line and in primary cells, and 4) the new drug has activity on single cell transport, establishing that it can mediate effects by augmenting anion transport at the plasma membrane, so that transcellular (as opposed to paracellular) effects on Cl⁻ transport across a cell monolayer or tissue can also be predicted.

Figure 3A:
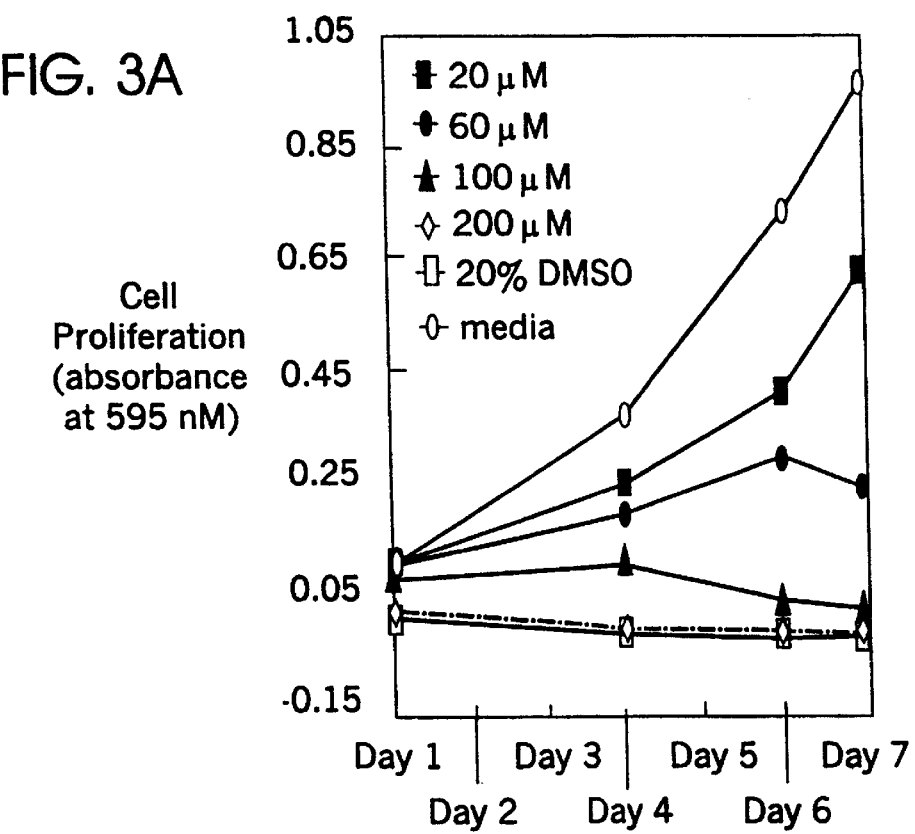
FIGS. 3A–3B show cyclic cAMP and growth characteristics of CF cells.
Figure 3B:
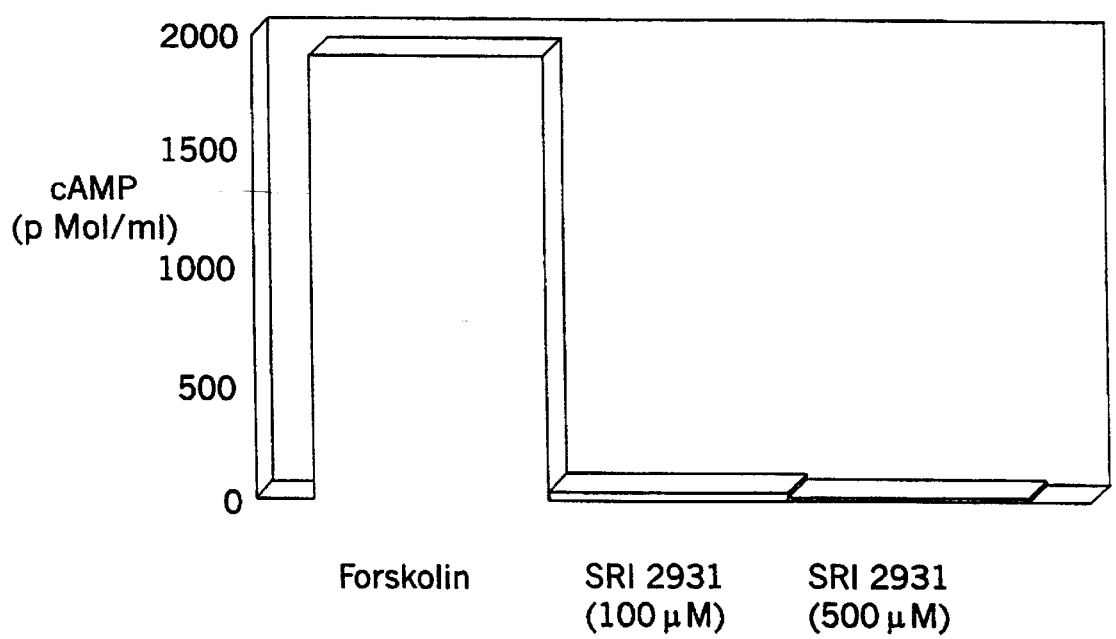

FIG. 3 shows that under the same conditions than anion transport is stimulated, no increase in cellular cAMP levels within cells can be measured (FIG. 3B), and CFPAC cells continue to proliferate even after several days of exposure to a drug that activates Cl⁻ secretion within minutes (FIG. 3A). Taken together, this data indicates that the effect of the compounds employed according to the present invention is unlikely to be cAMP-mediated and does not appear toxic to cells at the concentrations studies. In contrast to drugs such as ionomycin, the transient effects do not appear strongly dependent on extracellular $Ca^{2+}$, so it is unlikely that the compounds employed in the present invention act as a $Ca^{2+}$ ionophore or, for example, through non-specific effects on the cell membrane that would allow $Ca^{2+}$ influx. The activity is also different from drugs believed to act through cAMP-protein Kinase A such as milrinone or adenosine.

Test for Activation of Transepithelial Chloride Transport In CF Epithelial Cell Monolayers FIG. 4. Cl⁻ secretion in CFPAC-1 cells. CFPAC-1 cell monolayers were grown to confluency on permeable supports (Millipore) for 10 days. Filters were mounted in an Ussing chamber, and short circuit current measurement was carried out as previously described (Venglarik and Dawson, Am. J. Physiol. 251:C563–C570, 1986). Filters were bathed in Ringer's solution (in mM: 145 Na⁺, 5 K⁺, 124.8 Cl⁻, 1.2 $Ca^{2+}$, 1.2 $Mg^{2+}$, 25 $HCO_3$—, 4.2 $PO_4$, 10 glucose; pH=7.4) on the serosal surface and in a 6 mM Cl⁻ Ringer's solution (118.8 mM of Cl⁻ was replaced by the impermeant anion gluconate) on the mucosal surface. The compounds were screened using different concentrations of drugs and adding them to alternate surfaces of the filters (mucosal; serosal; mucosal and serosal). The effects of forskolin (10 µM), UTP (100 µM) CPX (100 µm) and duramycin (5 µm) were also studied.

Figure 5:
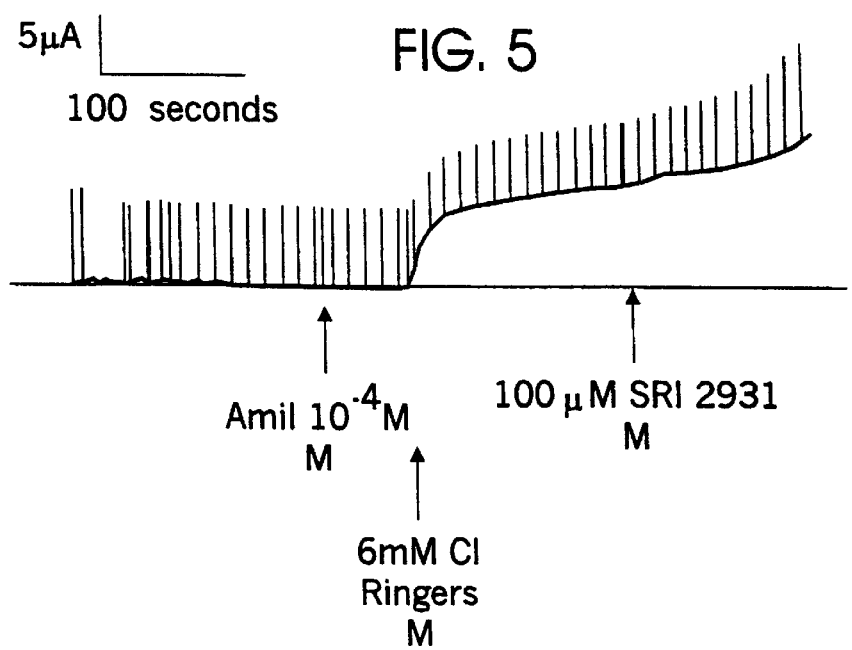
FIG. 5 illustrates $I_{Sc}$ response.
Figure 4A:
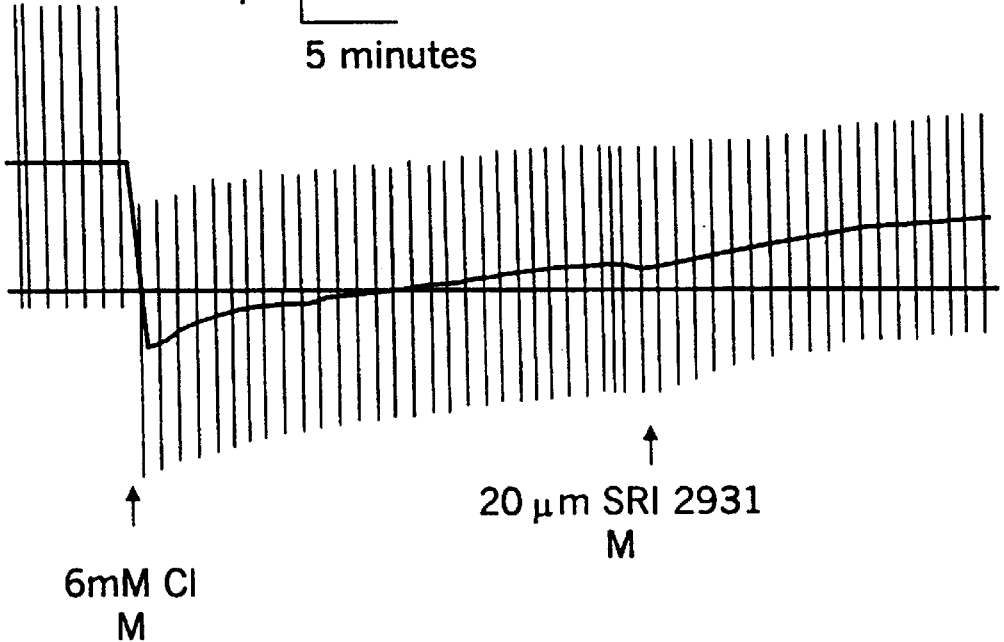
Figure 4B:
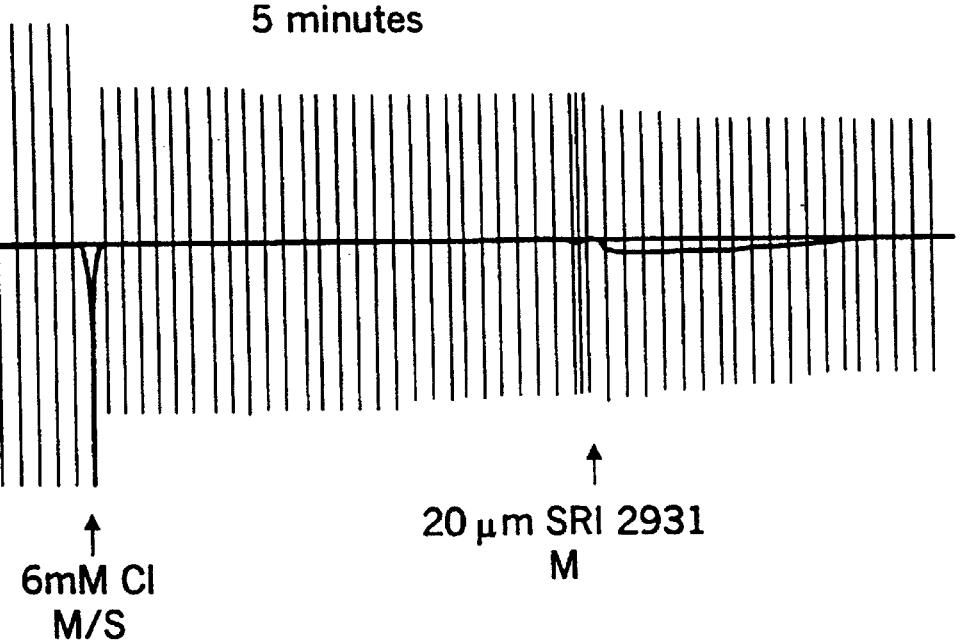
Figure 6A:
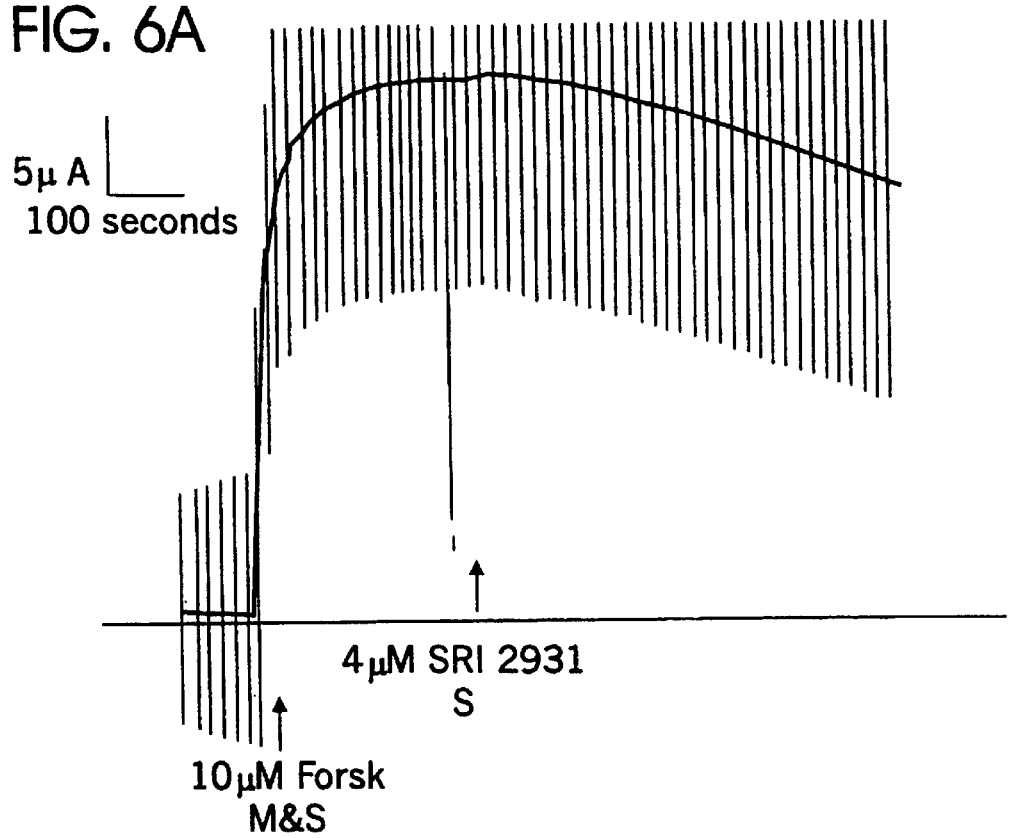
FIGS. 6A–6D show $I_{Sc}$ response in T84 colonic epithelial cells.
Figure 6B:
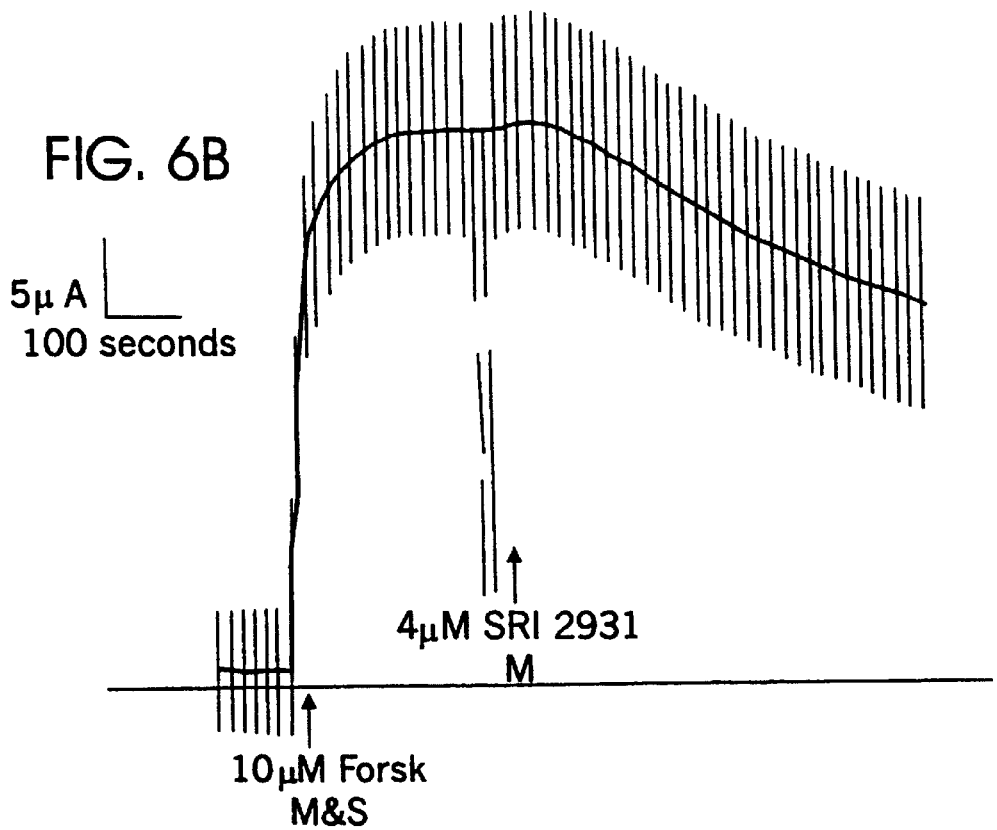
Figure 6C:
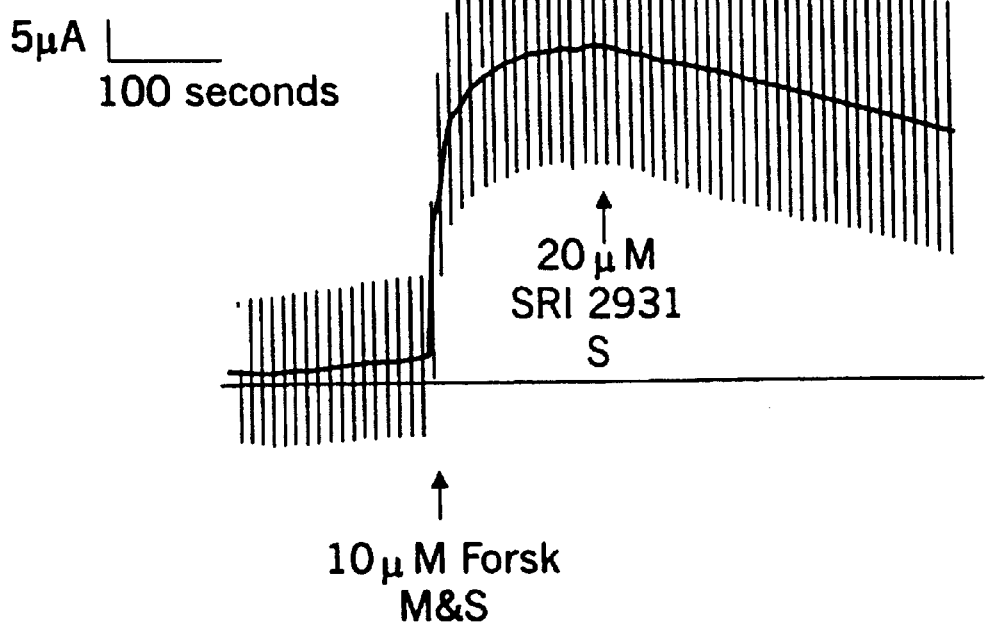
Figure 6D:
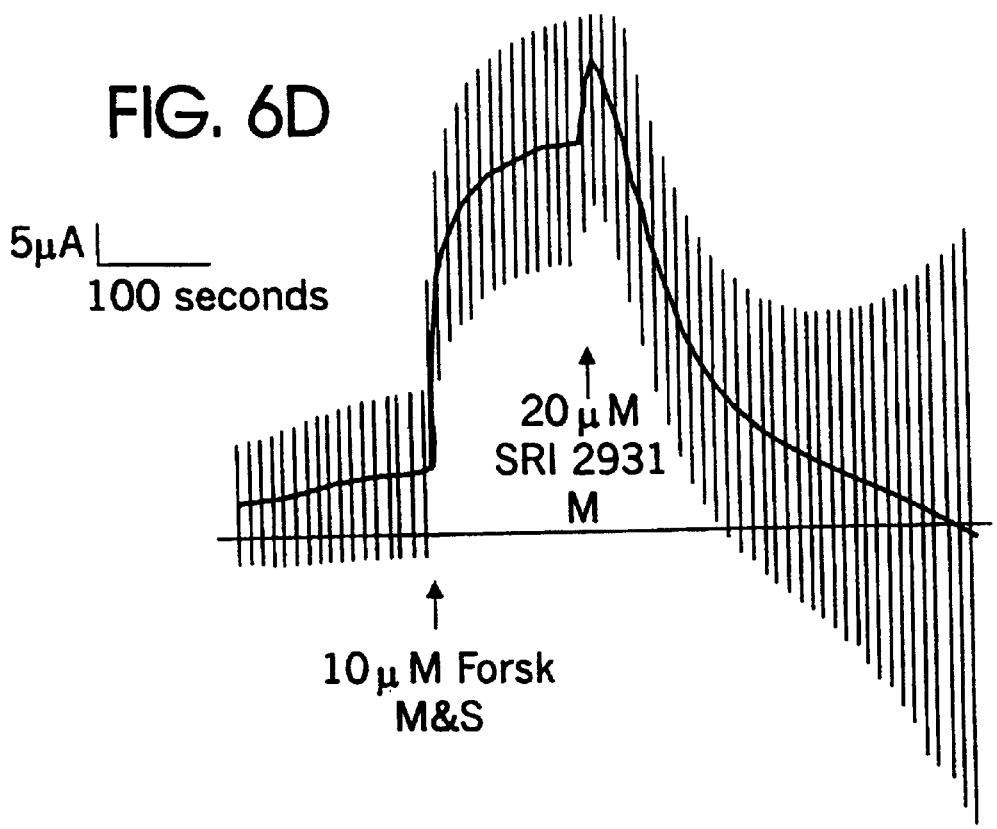
Figure 7A:
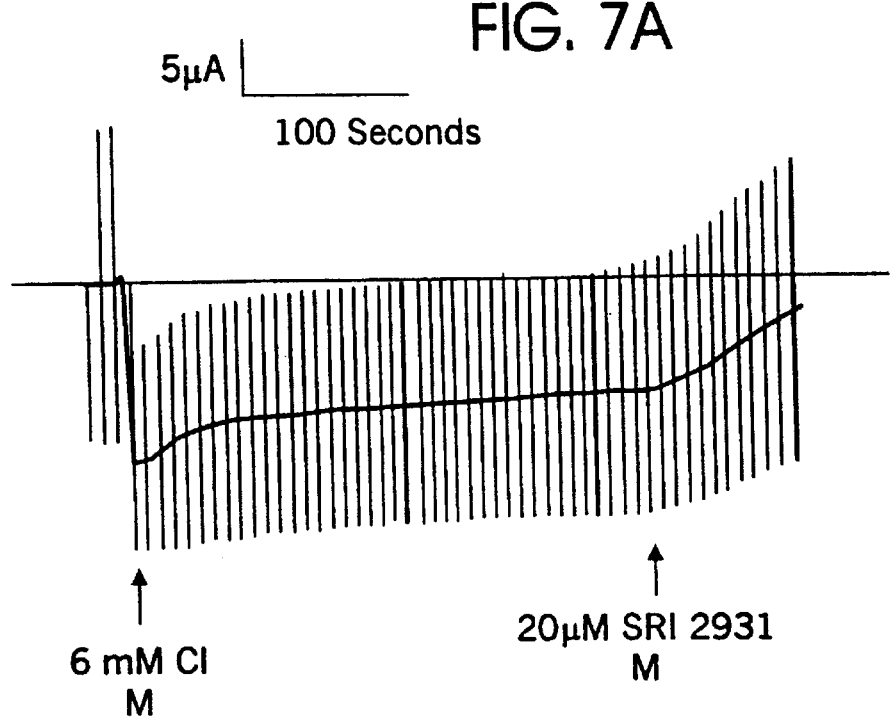
FIGS. 7A–7D show $I_{Sc}$ response in secretory epithelial cell monolayers.
Figure 7B:
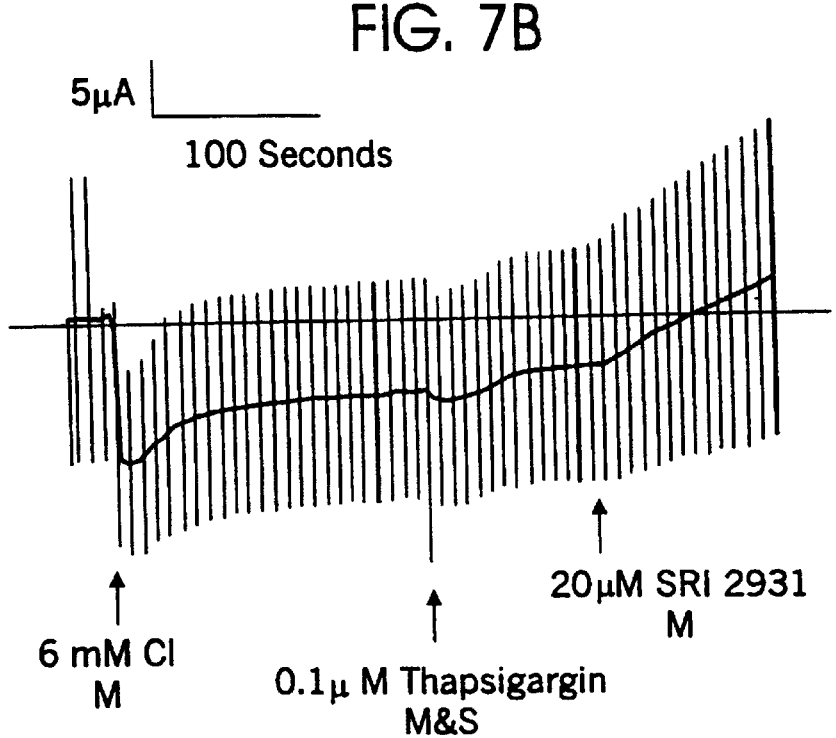
Figure 7C:
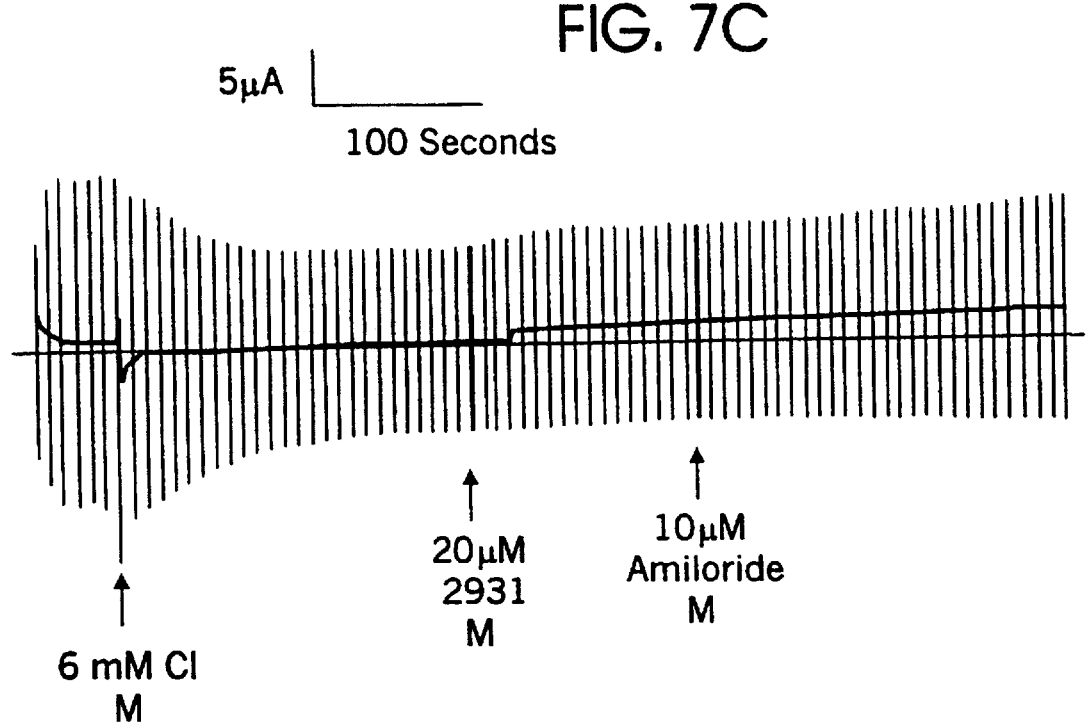
Figure 7D:
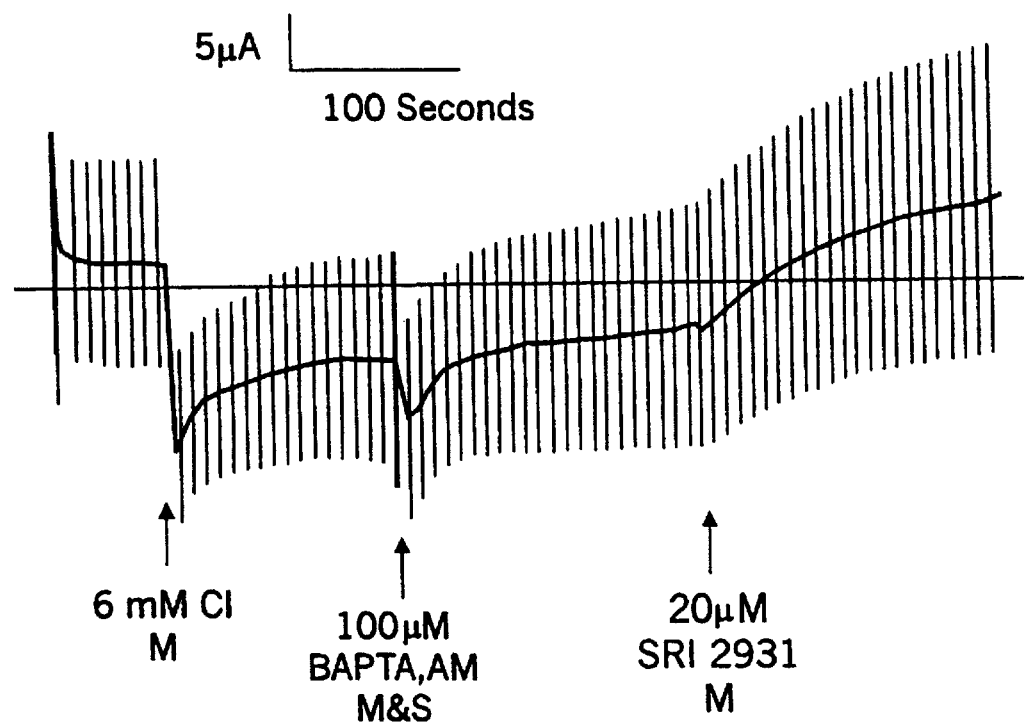
Figure 8A:
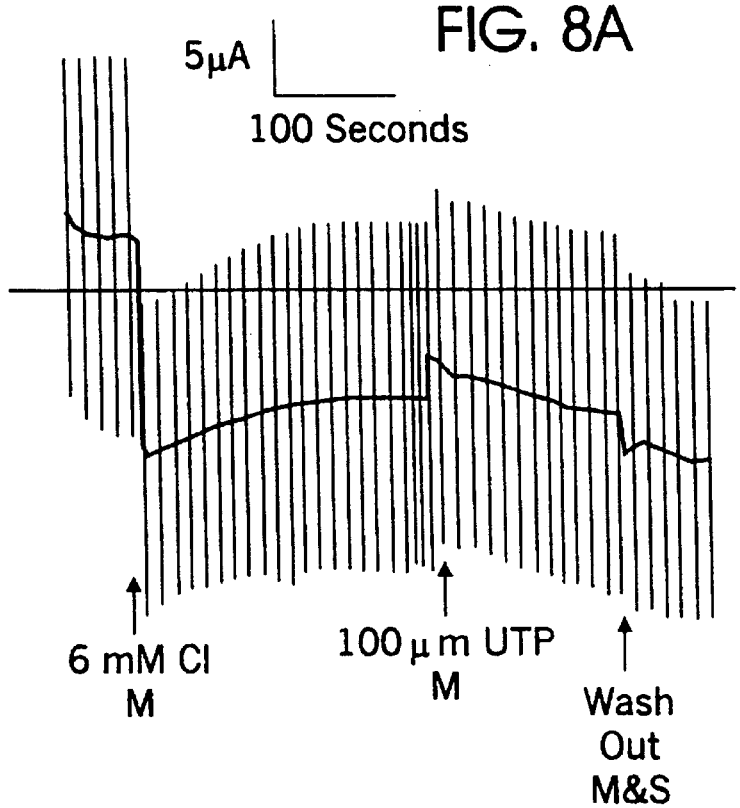
FIGS. 8A–8F show Cl⁻ secretion across polarized cells.
Figure 8B:
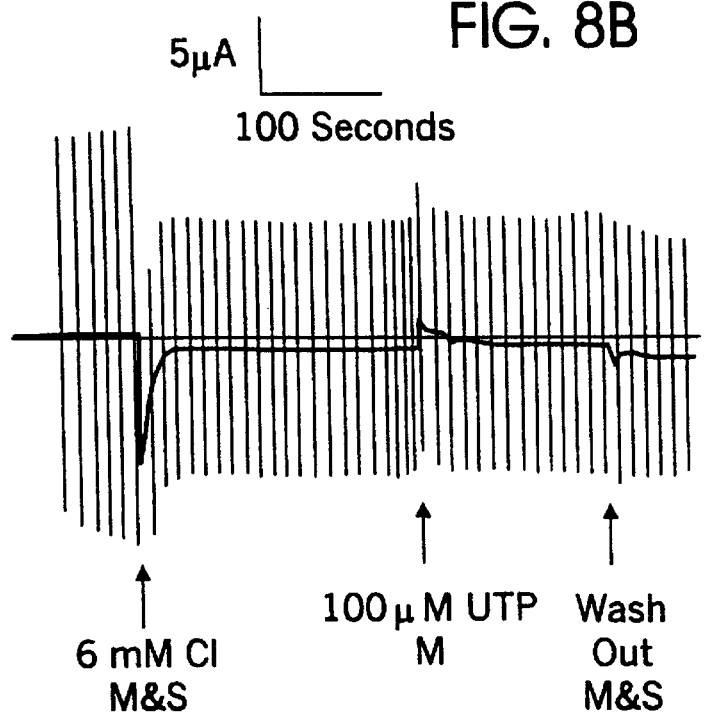
Figure 8C:
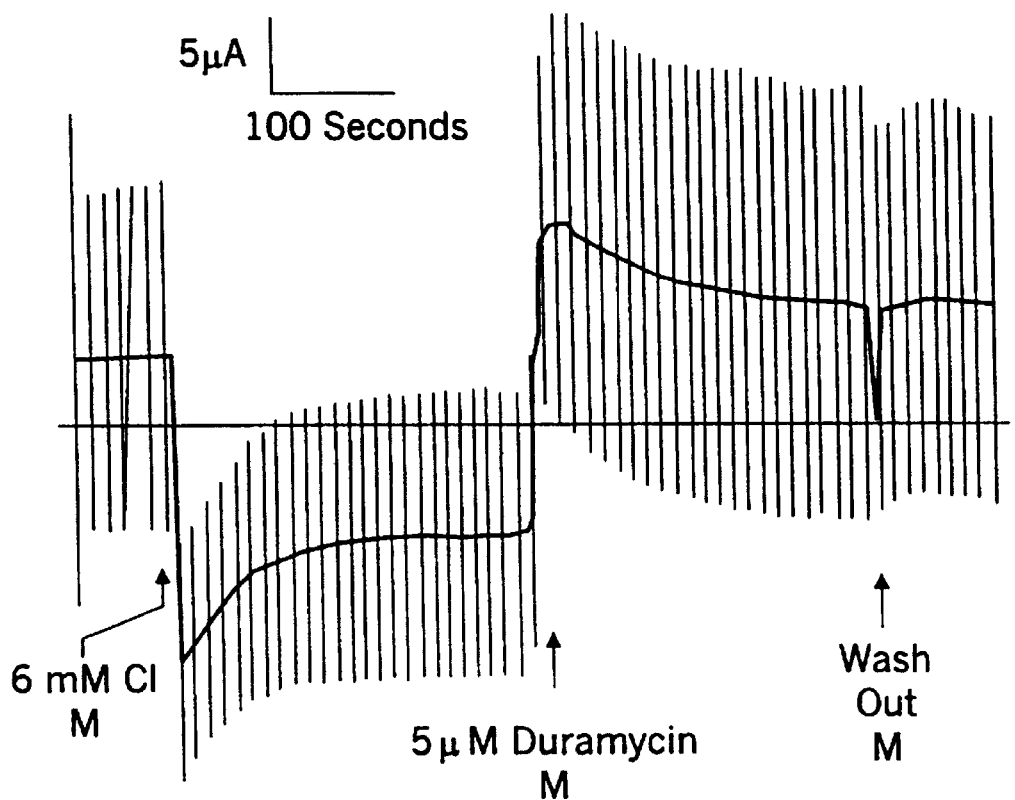
Figure 8D:
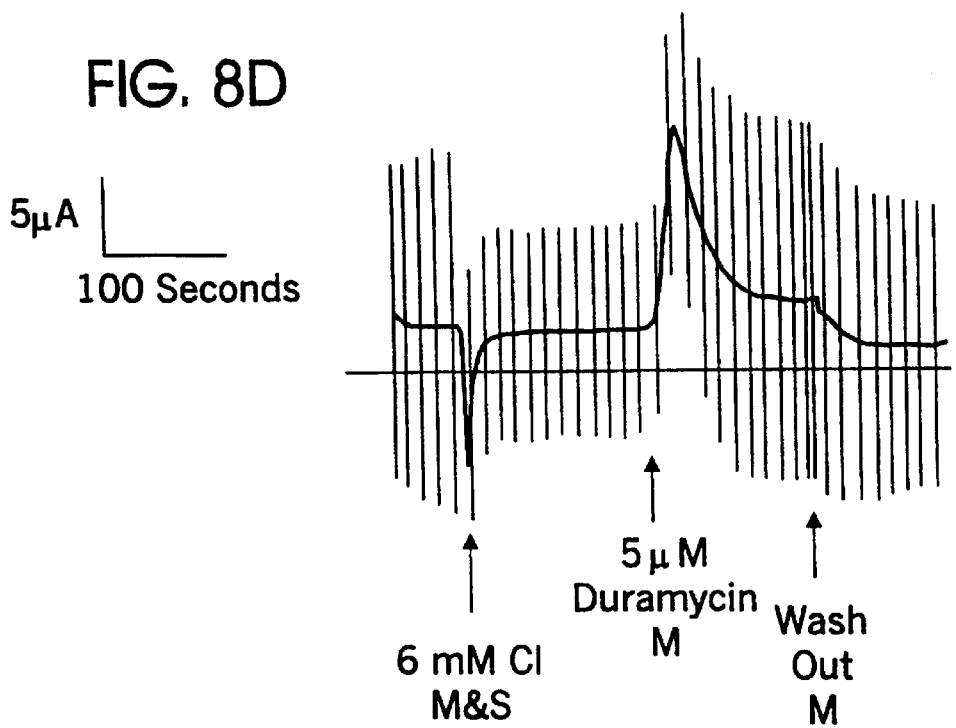
Figure 8E:
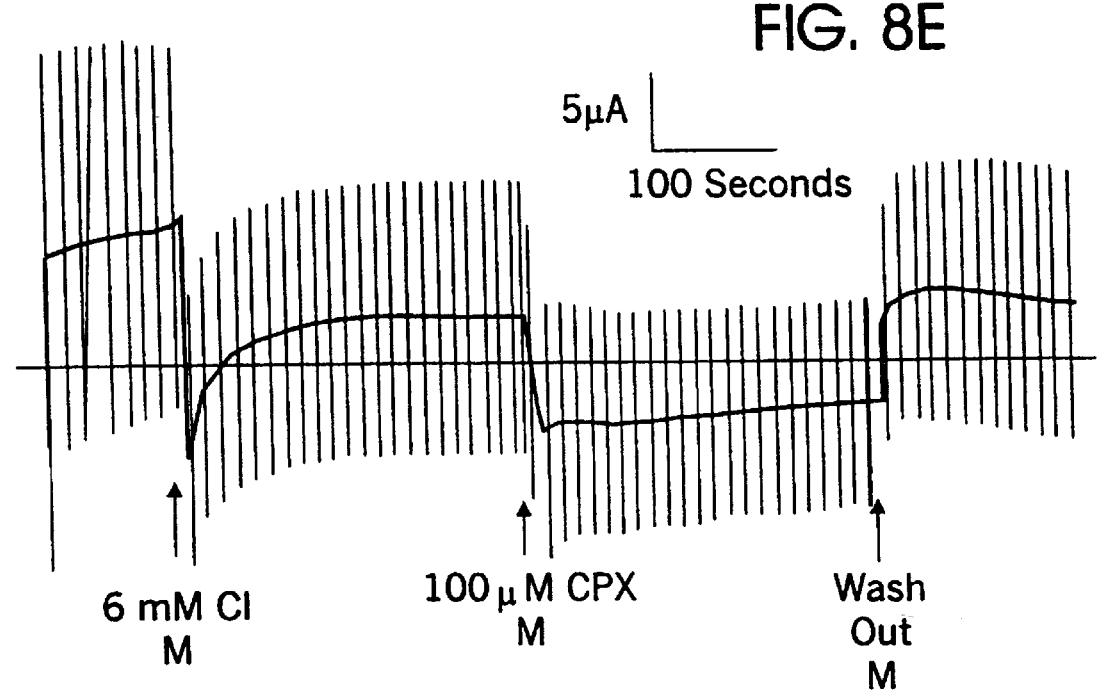
Figure 8F:
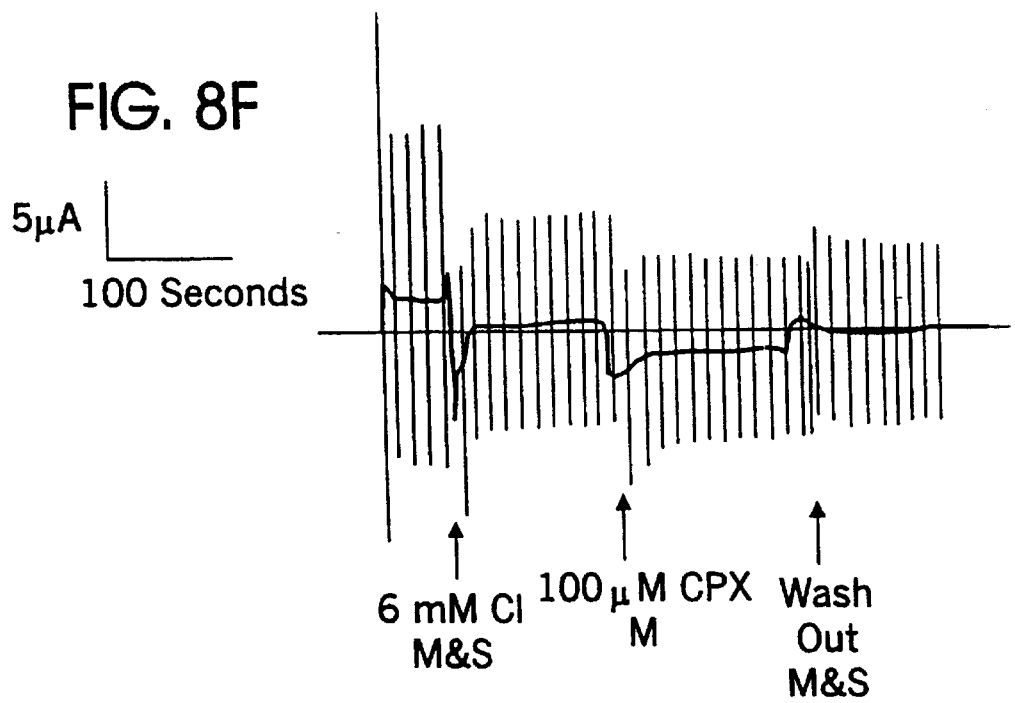

In order to test 5-diazoimidazol-4-carboxylic acid n-octyl ester in transepithelial Cl⁻ transport, CFPAC cells were grown as a low resistance monolayer on permeable supports. Explants of CF nasal polyps (primary airway epithelial cells) and control, non-CF colonic epithelial cells (T84) containing wild-type CFTR were also studied. In the presence of a serosal-to-mucosal Cl⁻ gradient, addition of the drug to the apical (but not basolateral) surface led to a strong $I_{sc}$ response in the direction of Cl⁻ secretion (FIG. 4A). The $I_{SC}$ is Cl⁻-dependent and was much less pronounced when Cl⁻ was omitted from the mucosal and serosal bathing solutions (FIG. 4B). The direction of $I_{SC}$ could be reversed by reversing the Cl⁻ gradient (i.e., from mucosal-to-serosal), supporting the notion that Cl⁻ transport was responsible for the $I_{SC}$ caused by the 5-diazoimidazol-4-carboxylic acid n-octyl esters (FIG. 4D). Similar $I_{SC}$ activation by this compound was also observed in cystic fibrosis primary airway epithelial cells (FIG. 5), and in T84 colonic epithelial cells (FIG. 6) grown as monolayers on permeable supports. The 5-diazoimidazol-4-carboxylic acid n-octyl ester augmented the maximal $I_{SC}$ activation caused by 10 µM forskolin, suggesting that it works through a mechanism different from cAMP activation and that the drug further augments the $I_{SC}$ present in (secretory) epithelial cell monolayers due to increased cAMP (FIG. 6). In other words, these experiments raise the possibility that Cl⁻ secretion effects of drugs such as adenosine, milrinone, IBMX, or forskolin might be increased by compounds employed in the present invention by a conjoint therapy treatment. Amiloride (10 µM) applied to the apical surface of CFPAC cells did not alter this response (suggesting that the effect is not mediated by $Na^{2+}$ reabsorption; note that CFPAC cells do not normally perform Na⁺ reabsorption as they are derived from a cell type (pancreatic ductular cells) that are not $Na^{2+}$ reabsorptive). BAPTA AM (100 µM, to deplete intracellular $Ca^{2+}$, and thapsagargin (0–1 µM, to prevent release of intracellular $Ca^{2+}$ stores) also had no effect on the 5-diazoimidazole-4-carboxylic acid n-octyl ester-induced $I_{SC}$ (FIG. 7). These results indicate that the compound acts through a mechanism different from previous modes of activating Cl⁻ secretion in CF cells, such as cyclic AMP or $Ca^{+2}$. The $I_{SC}$ was not likely to be caused by $HCO_3$-secretion, since an inhibitor of $HCO_3$-production (acetazolimide, 100 µM) did not inhibit the effect of the diazoimidazol. The activation of $I_{SC}$ also does not appear to require an imposed gradient across the cell monolayer. In symmetrical Ringer's lactate (equivalent NaCl on both sides of the monolayer), activation of $I_{SC}$ in the direction of Cl⁻ secretion was still present, indicating that cells remain active and able to maintain a gradient for Cl⁻ secretion after addition of the 5-diazoimidazol-4-carboxylic acid n-octyl ester. The $I_{SC}$ occurs after mucosal, but not serosal addition of the compound.

Simplified model of epithelial Cl⁻ secretion.

Epithelial cells accumulate Cl⁻ and K⁺ intracellularly by virtue of coordinated activity of a Na/K/2Cl co-transporter and the Na/K-ATPase in the basolateral membranes of Cl⁻ secreting epithelia. A strong electrochemical driving force (for the exit of K⁺ ions through basolateral K⁺ channels and the exit of Cl⁻ ions through apical Cl⁻ channels) exists in these cells in their resting state. Increases in cellular cAMP open both K⁺ and Cl⁻ channels in normal tissues, resulting in fluid and electrolyte (Cl⁻) secretion across the apical membrane and into the lumen. It is believed that the 5-diazoimidazol-4-carboxylic acid n-octyl ester works by directly augmenting the permeability of the apical membrane of polarized epithelial cells to ions such as Cl⁻. In particular, it augments anion permeability in lung, pancreas, and colonic epithelium by an anion efflux protocol (FIGS. 1 and 2). Second, the compound acts only at the apical, but not the basolateral cell surface in these cells (FIG. 4). Third, it does not appear to act through cell signalling pathways such as $Ca^{2+}$ or cAMP that are known to open epithelial Cl⁻ channels. Fourth, the effects are additive with another agent (forskolin) that raises cellular cAMP and increases the driving force across the apical membrane for Cl⁻ secretion. Each of these observations supports the belief that 5-diazoimidazol-4-carboxylic acid n-octyl ester directly and specifically activates Cl⁻ permeability in the apical membranes of human epithelial cells derived from many tissues.

The activity of 5-diazoimidazole-4-carboxylic acid n-octyl ester was of longer duration than other drugs (UTP, CPX, or duramycin) studied under the same conditions in CFPAC cells (FIG. 8). CPX or (100 μM) had an effect on transepithelial transport that did not suggest strong Cl⁻ secretion, even in the presence of a serosal-mucosal Cl⁻ gradient. Although the concentration of CPX used here was the same as that reported to activate Cl⁻ efflux for CFPAC cells, the predominant $I_{SC}$ was in a direction opposite to that expected for Cl⁻ secretion. UTP had a small, transient activation $I_{SC}$ in CFPAC cells, and duramycin, a drug believed to act through increased intracellular $Ca^{2+}$ confirmed a stronger, although transient, activation of $I_{SC}$ in the same system, again in a direction compatible with Cl⁻ secretion. UTP and CPX have both been used as part of clinical trials as Cl⁻ secretagogues in CF. 5-diazoimidazol-4-carboxylic acid n-octyl ester has more potent and prolonged effects than either of these drugs, is believed to work by a different mechanism, and is therefore expected to have substantial advantages over nay available compound for activating Cl⁻ secretions in CF tissues.

These results confirm activity of a Cl⁻-dependent $I_{sc}$ in CF epithelial cells treated with 5-diazoimidazol-4-carboxylic acid n-octyl ester. Drugs such as forskolin and CPX do not mediate Cl⁻ secretion in CF cells by this protocol, and UTP mediates a smaller, transient effect. Because the $I_{sc}$ could be reversed by switching the Cl⁻ concentration gradient, part of the effect could be paracellular. However, the direct effects of 5-diazoimidazol-4-carboxylic acid n-octyl ester on anion efflux in single cells independent of cellular junctions (FIG. 2) has been demonstrated in our experiments. Moreover, the $I_{sc}$ activation is also noted when symmetrical bathing solutions are present, indicating that an important part of the effect is due to a transcellular pathway. These tests establish that the compounds employed in this invention act as strong stimulators of anion transport in single CF cells and CF cell monolayers in vitro.

Figure 9A:
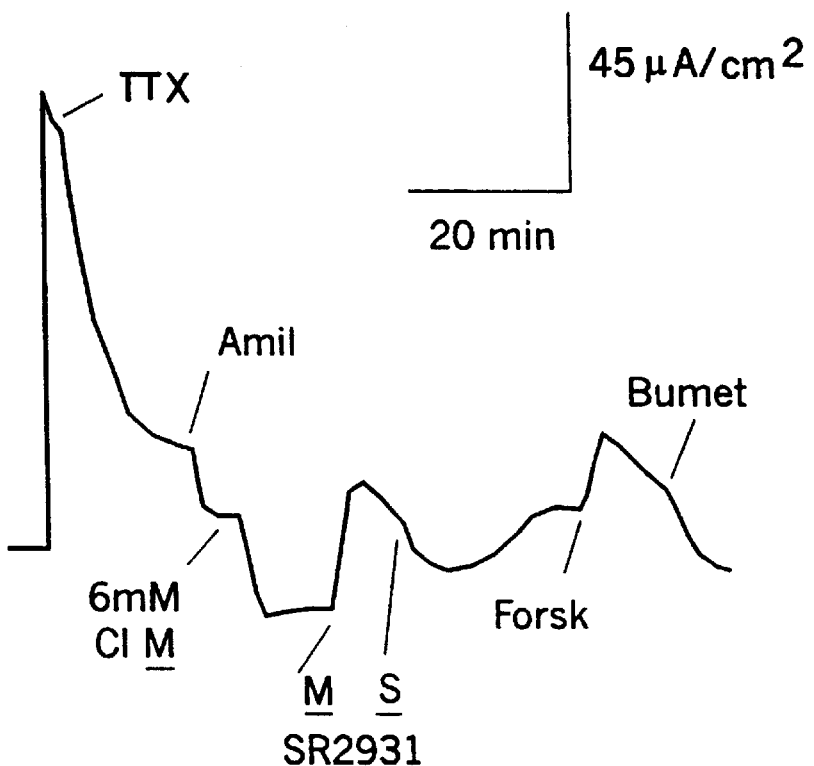
FIGS. 9A–9B show transport in CF mouse epithelia.
Figure 9B:
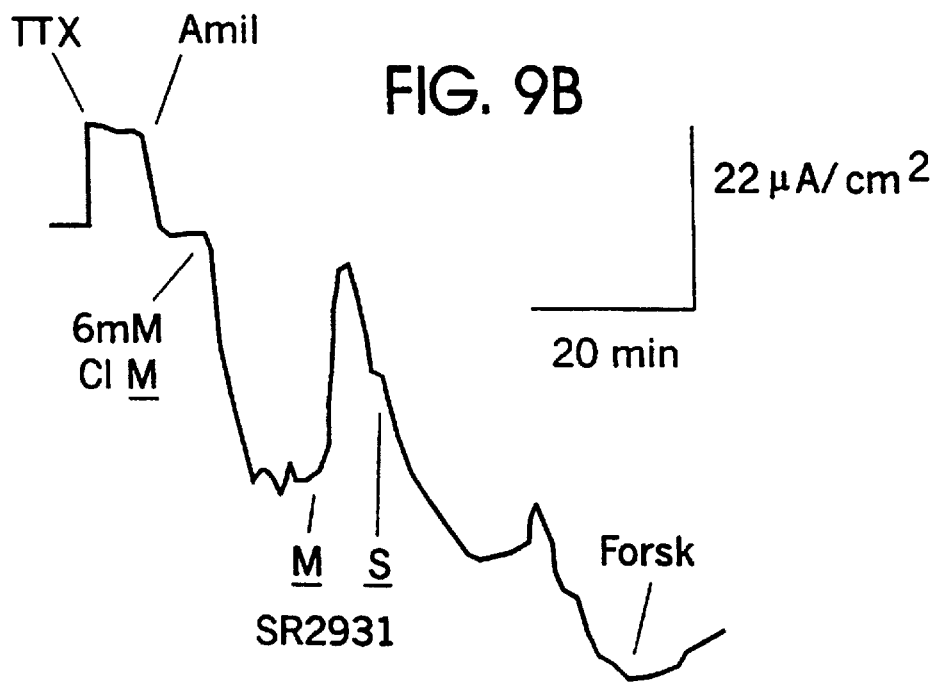

C.4. Studies in Diazoimidazole and Chloride Secretion in Intact Tissues 5-diazoimidazole-4-carboxylic acid n-octyl ester activates $I_{sc}$ across a mouse intestine when added to the mucosal surface. The activation is similar to that observed for primary CF airway cells and CFPAC cell monolayers, and occurs in normal mice (A) and in ΔF508 CFTR transgenic mice (B) (FIG. 9). $I_{sc}$ activation is also observed in CFTR knock out (−/−) mice (data not shown), indicating that the action elicited by compound does not require expression of either wild-type or mutant CFTR protein.

FIG. 9. Transport in CF mouse intestinal epithelia.

Small sections of mouse colon from both wild-type and CF knockout mice were mounted in Ussing chambers, and $I_{sc}$ measurements were recorded as described above. Both mucosal and serosal surfaces were bathed in regular Ringer's solution, and TTX ($1.54 \times 10^{-3}$ μM) was added to the serosal side of the tissue. After a steady-state had been obtained, amiloride ($10^{-4}$ M) was added to the mucosal surface. Both sides were then bathed with regular Ringer's. A Cl⁻ gradient was established by bathing the mucosal surface with a 6 mM Cl⁻ solution. 5-diazoimidazole-4-carboxylic acid n-octyl ester (100 μM) was added first to the mucosal and then the serosal surface of the mounted tissue (FIG. 9).

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the invention concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method for promoting Cl⁻ secretion in a patient in need thereof which comprises administering to said patient a composition comprising a pharmaceutically acceptable carrier and an amount effective for promoting or activating Cl⁻ secretion of a compound represented by the formula:

wherein A is an imidazole;

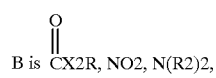

X2 is O, NH, NR, CH₂, CHR or CR₂,
each R individually is alkyl, cycloalkyl, aryl, alkaryl and aralkyl,
each R2 individually is H, alkyl, cycloalkyl, aryl, alkaryl and aralkyl;
Y is halogen; alkylthio group or nitrogenous moiety selected from the group consisting of $N_2$, $N_3$, $NO_2$, $NH_2$, CN, and NCS.

2. The method of claim 1 wherein the alkyl moieties of said R and $R^2$ groups contain 1–22 carbon atoms and the aryl moieties of said R groups contain 6–14 carbon atoms.

3. The method of claim 1 wherein each R individually is selected from the group consisting of methyl, ethyl, isopropyl, n-butyl, hexyl, hexenyl, octyl, decyl, dodecyl, phenyl, benzyl and phenethyl.

4. The method of claim 1 wherein said compound is 5-diazoimidazole-4-carboxylic acid n-octyl ester.

5. The method of claim 1 wherein said compound is selected from the group of compounds represented by the formulae:

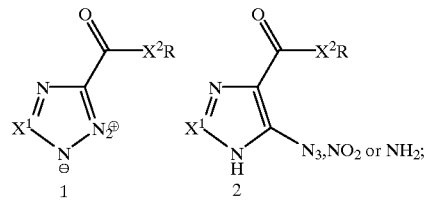

wherein $X^1$ is CH or CR.

6. A method for treating a patient suffering from cystic fibrosis which comprises administering to said patient a composition comprising a pharmaceutically acceptable carrier and an amount effective for promoting or activating Cl⁻ secretion of a compound represented by the formula:

wherein A is an imidazole;

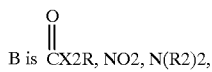

X2 is O, NH, NR, CH$_2$, CHR or CH$_2$,
  each R individually is alkyl, cycloalkyl, aryl, alkaryl and aralkyl,
  each R2 individually is H, alkyl, cycloalkyl, aryl, alkaryl and aralkyl;
Y is halogen; alkylthio group or nitrogenous moiety selected from the group consisting of N$_2$, N$_3$, N$_2$, NH$_2$, CN, and NCS.

7. The method of claim 6 wherein the alkyl moieties of said R and R$^2$ groups contain 1–22 carbon atoms and the aryl moieties of said R groups contain 6–22 carbon atoms.

8. The method of claim 6 wherein each R individually is selected from the group consisting of methyl, ethyl, isopropyl, n-butyl, hexyl, hexenyl, octyl, decyl, dodecyl, phenyl, benzyl and phenethyl.

9. The method of claim 6 wherein said compound is 5-diazoimidazole-4-carboxylic acid n-octyl ester.

10. The method of claim 6 wherein said compound is selected from the group of compounds represented by the formulae:

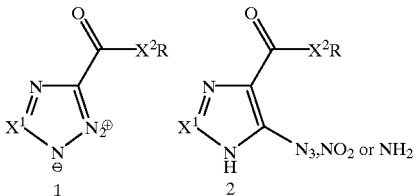

; wherein X$^1$ is CH or CR.

* * * * *